(12) United States Patent
Ergen et al.

(10) Patent No.: US 11,615,887 B2
(45) Date of Patent: Mar. 28, 2023

(54) METHOD AND SYSTEM FOR CONTACT TRACING USING A SOFTWARE DEVELOPMENT KIT (SDK) INTEGRATED INTO CLIENT DEVICES

(71) Applicant: Ambeent Wireless, Istanbul (TR)

(72) Inventors: Mustafa Ergen, Istanbul (TR); Onur Ergen, Istanbul (TR); Mehmet Fatih Tuysuz, Istanbul (TR)

(73) Assignee: AMBEENT INC., Yuba City, CA (US)

( * ) Notice: Subject to any disclaimer, the term of this patent is extended or adjusted under 35 U.S.C. 154(b) by 468 days.

(21) Appl. No.: 16/900,484

(22) Filed: Jun. 12, 2020

(65) Prior Publication Data
US 2021/0391072 A1 Dec. 16, 2021

(51) Int. Cl.
| | |
|---|---|
| G06Q 10/00 | (2012.01) |
| G16H 40/67 | (2018.01) |
| G06F 8/20 | (2018.01) |
| H04W 4/029 | (2018.01) |

(52) U.S. Cl.
CPC ............... *G16H 40/67* (2018.01); *G06F 8/20* (2013.01); *H04W 4/029* (2018.02)

(58) Field of Classification Search
CPC ........ G16H 40/67; G16H 50/20; G16H 50/80; G06F 8/20; H04W 4/029; H04W 4/023
USPC ....................................... 705/2, 41; 455/312
See application file for complete search history.

(56) References Cited

U.S. PATENT DOCUMENTS

| | | |
|---|---|---|
| 2012/0303446 A1 | 11/2012 | Busch |
| 2015/0105096 A1 | 4/2015 | Chowdhury et al. |
| 2015/0269267 A1 | 9/2015 | Ekambaram et al. |
| 2017/0024531 A1 | 1/2017 | Malaviya |
| 2018/0293870 A1 | 10/2018 | Lejeune, Jr. |
| 2021/0313074 A1* | 10/2021 | Mesirow ................ G16H 10/40 |

OTHER PUBLICATIONS

International Search Report and Written Opinion in PCT/US2021/036981 dated Sep. 8, 2021.

* cited by examiner

*Primary Examiner* — Marcos Batista
(74) *Attorney, Agent, or Firm* — Chip Law Group

(57) ABSTRACT

The invention generally relates to a method and system for utilizing an Artificial Intelligence (AI)-based technology for tracking human mobility patterns and contact points, via a Software Development Kit (SDK) integrated into client device applications. The SDK performs contact tracing by recording past and current signal data/measurements of Wi-Fi access points encountered by a client device and stores these measurements in a local memory of the client device. The SDK further analyses the recorded past and current signal data/measurements of the Wi-Fi access points using an AI module to derive mobility patterns of user of the client device. The AI module of the SDK then identifies other client devices that the client device may have encountered based on analyzing the mobility patterns of the user of the client device and the recorded past and current signal data/measurements and via performing Wi-Fi network sniffing.

20 Claims, 4 Drawing Sheets

METHOD AND SYSTEM FOR CONTACT TRACING USING A SOFTWARE DEVELOPMENT KIT (SDK) INTEGRATED INTO CLIENT DEVICES

FIELD OF THE INVENTION

The invention generally relates to contact tracing with client devices (for example, mobile devices) leveraging wireless communications. Specifically, the invention relates to a method and system for using an Artificial Intelligence (AI)-based technology for tracking human mobility patterns and contact points for the purpose of contact tracing, making use of wireless signals sent/received via a Software Development Kit (SDK) integrated into any client device application.

BACKGROUND OF THE INVENTION

Contact tracing or contact investigation has been employed in numerous fields for purposes such as, but not limited to, detection of epidemic/pandemic cases and prevention of their spread, tracking crime or criminals, and for location-based advertising.

In the field of epidemiology, contact tracing has traditionally been a manual process for tracking/identifying individuals of a community who encountered an infected person for purposes of screening, diagnosis, and limiting further transmission of infections/contagions. Case and contact identification are critical for effective epidemic monitoring and response, and vital for governments to provide clear information to prevent panic in society. Early identification of cases and contacts prevents the virus from spreading and allows for earlier treatment. However, it is challenging and costly to trace tens of thousands of contacts a day across populations.

With the rapid growth in communication technologies, client devices with wireless communication support offer fast and effective solutions for the purpose of contact tracing, by tracking human mobility patterns and contact points for effective epidemic monitoring and prevention of virus from spreading. The client devices may include, but need not be limited to, mobile devices, smart phones, tablets, handheld computers, and wearable devices. These client devices leverage wireless communication technologies such as, but not limited to, Bluetooth low energy, wireless local area network (WLAN), Wi-Fi networks, and Near Field Communication (NFC), to transmit/receive signals for detecting other devices in close proximity.

Erstwhile techniques for contact tracing require extensive and costly set up and cannot be easily launched across governments, service providers and enterprise infrastructures. Furthermore, using Global Positioning System (GPS) data as part of contact tracing in these techniques to locate mobile phone users at a large scale may create noise leading to reduced efficiency and false positives. Given that transmission is more likely to take place in environments where there are public Wi-Fi hotspots available such as, but not limited to, cafes, malls, and buses, these techniques do not entirely focus on location data centered around such areas.

Thus, there exists a need for an improved method and system that provides for faster and reliable contact tracing leveraging Wi-Fi network signals, and effective communication of the information with relevant entities during emergency situations to minimize casualties.

BRIEF DESCRIPTION OF THE FIGURES

The accompanying figures where like reference numerals refer to identical or functionally similar elements throughout the separate views and which together with the detailed description below are incorporated in and form part of the specification, serve to further illustrate various embodiments and to explain various principles and advantages all in accordance with the invention.

Figure 1:
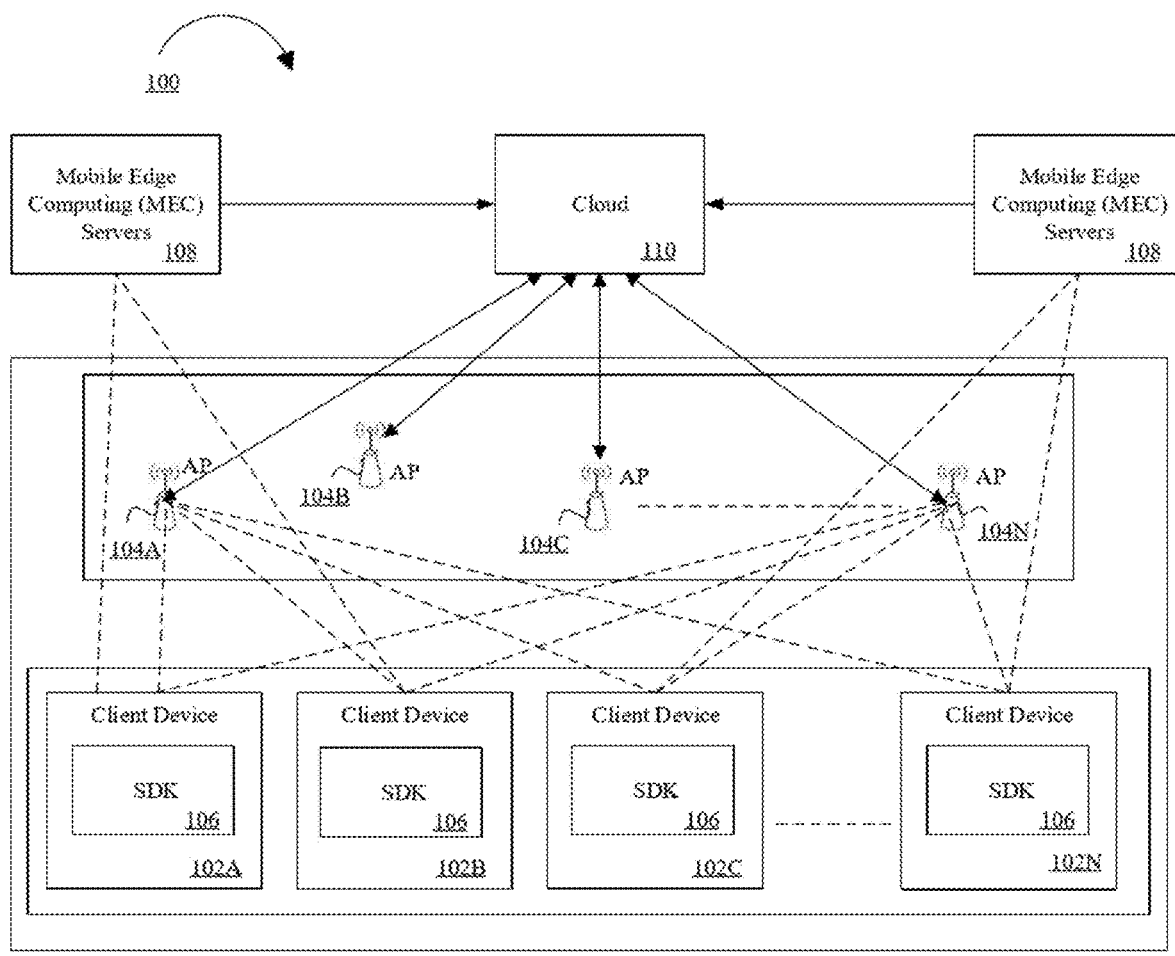
FIG. 1 illustrates a Wi-Fi network with different entities to enable contact tracing and information sharing in accordance with an embodiment of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF THE INVENTION

Before describing in detail embodiments that are in accordance with the invention, it should be observed that the embodiments reside primarily in combinations of method steps and system components for using an Artificial Intelligence (AI)-based technology for tracking human mobility patterns and contact points for the purpose of contact tracing, making use of wireless signals sent/received via a Software Development Kit (SDK) integrated into any client device application.

Accordingly, the system components and method steps have been represented where appropriate by conventional symbols in the drawings, showing only those specific details that are pertinent to understanding the embodiments of the invention so as not to obscure the disclosure with details that will be readily apparent to those of ordinary skill in the art having the benefit of the description herein.

The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language). The term coupled, as used herein, is defined as connected, although not necessarily directly, and not necessarily mechanically. The terms program, software application, and the like as used herein, are defined as a sequence of instructions designed for execution on a computer system. A program, computer program, or software application may include a subroutine, a function, a procedure, an object method, an object implementation, an executable application, an applet, a servlet, a source code, an object code, a shared library/dynamic load library and/or other sequence of instructions designed for execution on a computer system.

Various embodiments of the invention disclose a method and system for contact tracing using a Software Development Kit (SDK) integrated into each client device of a plurality of client devices in a Wi-Fi network. The SDK in a client device records past and current signal data/measurements of one or more Wi-Fi access points encountered by the client device and stores these measurements in a local memory of the client device. In an embodiment, the SDK accesses operating system of the one or more Wi-Fi access points encountered by the client device to record earlier signal measurements of the one or more Wi-Fi access points. The SDK further analyses the recorded past and current signal data/measurements of the one or more Wi-Fi access points using an AI module to derive mobility patterns of a user of the client device. The AI module of the SDK then identifies other client devices that the client device may have encountered based on analyzing the mobility patterns of the user of the client device and the recorded past and current signal data/measurements of the one or more Wi-Fi access points. For instance, the SDK identifies a total number of client devices connected to the one or more Wi-Fi access points, a number of other client devices the one or more Wi-Fi access points received signals from, MAC addresses of the connected client devices and the other client devices, and how long each client device stayed in close proximity to the one or more Wi-Fi access points. The SDK also performs network sniffing over a Wi-Fi interface to identify mobile/fixed users of other client devices in close proximity/vicinity to the client device but not connected to the same Wi-Fi access point as the client device, and records the information related to the other client devices in the local memory if received signal strength from the other client devices exceeds a predetermined threshold value. Further, the AI module of the SDK enables pairing of the client device with users of client devices in the vicinity of the same Wi-Fi access point with respect to certain time periods for receiving/transmitting information for contact tracing, and information is also transmitted from the client devices to cloud or relevant authorities, depending on the authorization.

FIG. 1 illustrates a Wi-Fi network 100 with different entities to enable contact tracing and information sharing in accordance with an embodiment of the invention.

As illustrated in FIG. 1, Wi-Fi network 100 includes a plurality of client devices 102A-102N and a plurality of Wi-Fi access points 104A-104N. Wi-Fi network 100 can be, but need not be limited to, a 5G autonomic network.

Plurality of client devices 102A-102N can be, but need not be limited to, user computing devices such as, but not limited to, a mobile device, a personal digital assistant, a computer, a laptop, a smart phone and a tablet. Plurality of Wi-Fi access points 104A-104N are deployed in places such as, but not limited to, homes, enterprises, and public spaces.

Each client device of plurality of client devices 102A-102N further includes a Software Development Kit (SDK) 106 which utilizes an AI-based technology to perform contact tracing by tracking human mobility patterns and contact points, making use of Wi-Fi signals sent/received via SDK 106. SDK 106 can be integrated into any client device application such as, but not limited to, a mobile application.

Using SDK 106, a client device 102A of plurality of client devices 102A-102N tracks and records signals/measurements of one or more Wi-Fi access points of plurality of Wi-Fi access points 104A-104N in vicinity of the client device. SDK 106 maintains a list of Wi-Fi access points encountered by client device 102A in a local memory of client device 102A. SDK 106 uses the AI-based technology to analyze the recorded signals/measurements to identify a list of other client devices that client device 102A encountered, for contact tracing. In addition, SDK 106 also performs sniffing to identify other client devices in the vicinity of client device 102A over wireless interfaces such as, but not limited to, Wi-Fi and Bluetooth, to identify other mobile/fixed users who are in close proximity to client device 102A, but not connected to the same Wi-Fi access point as client device 102A.

Furthermore, the encountered Wi-Fi access points are also assigned with locations by SDK 106 based on a small number of GPS samples taken from client device 102A. For contact tracing, SDK 106 pairs users of client devices in the vicinity of the same Wi-Fi access point/router with respect to certain time periods for receiving/transmitting information.

Any data captured/processed/obtained by SDK 106 is encrypted first and stored locally on client device 102A for a certain period. The information related to user of client device 102A is then submitted to users of other client devices in the vicinity only under certain conditions, either by client device 102A itself, or by Mobile Edge Computing (MEC) servers 108 located close to client device 102A. The information is also stored on cloud 110 and is accessible only to authorized people. Various modules of SDK 106 are further described in detail in conjunction with FIG. 2.

Figure 2:
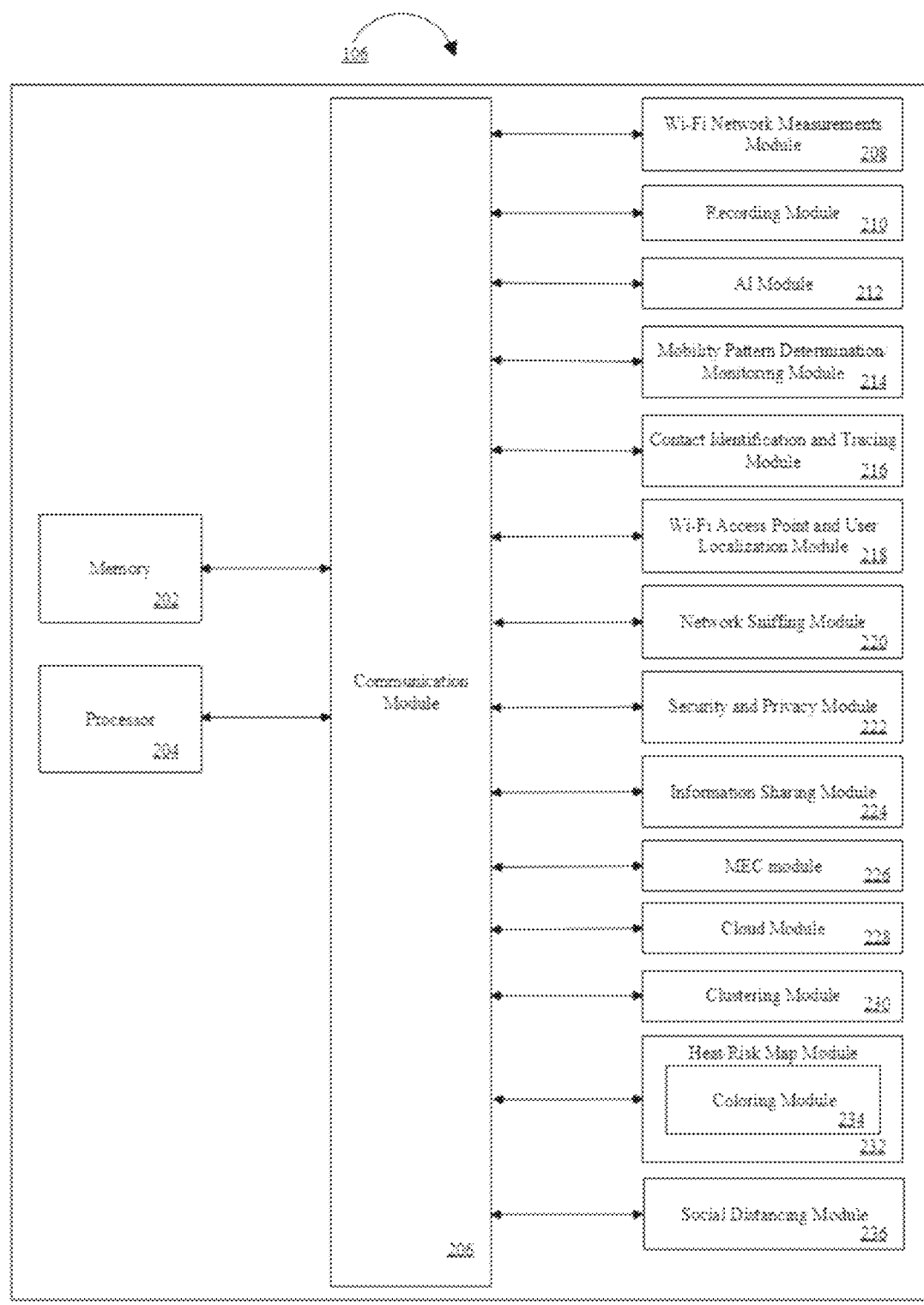
FIG. 2 illustrates various modules of a Software Development Kit (SDK) integrated into each client device of a plurality of client devices for contact tracing and information sharing in accordance with an embodiment of the invention.

FIG. 2 illustrates various modules of SDK 106 integrated into each client device of plurality of client devices 102A-102N for contact tracing and information sharing in accordance with an embodiment of the invention.

As illustrated in FIG. 2, SDK 106 comprises a memory 202 and a processor 204 communicatively coupled to memory 202. Memory 202 and processor 204 further communicate with various modules of SDK 106 via a communication module 206.

Communication module 206 may be configured to transmit data between modules, engines, databases, memories, and other components of SDK 106 for use in performing the functions discussed herein. Communication module 206 may include one or more communication types and utilizes various communication methods for communication within SDK 106.

For contact tracing, SDK 106 includes a Wi-Fi network measurements module 208 for tracking past and current signal data/measurements of one or more Wi-Fi access points of plurality of Wi-Fi access points 104A-104N encountered by a client device 102A of plurality of client devices 102A-102N and records these measurements in a local memory of client device 102A using a recording module 210. Wi-Fi network measurements module 208 further accesses operating system of the one or more Wi-Fi access points to record earlier signal measurements of the one or more Wi-Fi access points in the local memory of client device 102A using recording module 210. In an embodiment, a Wi-Fi access point owner and guest users having the password of the one or more Wi-Fi access points can access their operating systems to record earlier measurements of the one or more Wi-Fi access points.

SDK 106 further includes an AI module 212 for analyzing the recorded past and current signal data/measurements of the one or more Wi-Fi access points to derive mobility patterns of the user of client device 102A using a mobility pattern determination/monitoring module 214.

AI module 212 then identifies one or more other client devices of plurality of client devices 102A-102N that is/was in close proximity to client device 102A based on the analysis of the recorded past and current signal data/measurements of the one or more Wi-Fi access points and derived mobility patterns of the user of client device 102A. Using AI module 212, SDK 106 is able to identify a total number of client devices connected to the one or more Wi-Fi access points, a number of client devices the one or more Wi-Fi access points receives signals from, MAC addresses of those client devices in close proximity to client device 102A, and how long each client device stayed in close proximity to the one or more Wi-Fi access points.

Further, SDK 106 includes a contact identification and tracing module 216 which enables client device 102A maintain a list of one or more Wi-Fi access points it hears and is connected to, in its local memory based on processing/analyzing past and current signal data/measurements of the one or more Wi-Fi access points and mobility patterns of client device 102A.

SDK 106 also includes a Wi-Fi access point and user localization module 218 which assigns locations to the one or more Wi-Fi access points encountered by client device 102A based on a small number of GPS samples taken from the client devices in close proximity to the one or more Wi-Fi access points. Wi-Fi access point and user localization module 218 then uses these Wi-Fi access points as fixed beacons to predict other users' locations. Thus, Wi-Fi access point and user localization module 218 provides exact location of each Wi-Fi access point, whether it is public or private.

In an embodiment, client device 102A can have access to the information on other client devices in close proximity to the one or more Wi-Fi access points without having the Wi-Fi access point passwords, in case an additional SDK 106 is installed in the one or more Wi-Fi access points. The one or more Wi-Fi access points can then broadcast the required information.

SDK 106 also includes a network sniffing module 220 which performs sniffing over a wireless interface such as, but not limited to, Wi-Fi and Bluetooth, to identify mobile/fixed users of one or more client devices of plurality of client devices 102A-102N in close proximity/vicinity to client device 102A but not connected to the same Wi-Fi access point as client device 102A. Recording module 210 then records the information related to the one or more client devices in the local memory of client device 102A if received signal strength from the one or more client devices exceeds a predetermined threshold value. For example, using network sniffing module 220, client device 102A is able to identify users who are within 2 meters (via Bluetooth) or within 5-10 meters (via Wi-Fi with a received signal strength (RSS) threshold) of each other for more than y seconds (for example, 30 seconds). Further, while performing the sniffing operation on the Wi-Fi interface, if only the received signal strength obtained from other client devices in the vicinity of client device 102A is above a threshold value, contact identification and tracing module 216 includes these client devices in the pairing group and stores information related to these client devices in the local memory of client device 102A using recording module 210.

Network sniffing module 220 further identifies phone numbers of client device owners in close proximity to client device 102A along with other relevant information such as, but not limited to, name, age, nationality and MAC addresses of the client devices, in case each of the client devices is running SDK 106.

SDK 106 also includes a security and privacy module 222 which encrypts data captured by SDK 106 and stores it locally on client device 102A for a certain period of time. During installation, only client device 102A and its MAC address is required and no other data such as name, location, contact list, or address book is collected. Security and privacy module 222 enable data logs to be stored locally on client device 102 with cryptographically generated temporary IDs. The data logs are extracted only when needed by authorities for contact tracing.

Further, the data logs are shared securely only under certain circumstances via an information sharing module 224. AI module 212 enables pairing of users of client devices that are in the vicinity of the same Wi-Fi access point with respect to certain time periods, for receiving/transmitting information for the purpose of contact tracing via information sharing module 224.

Information sharing related to client device 102 A can include, but need not be limited to, the following: information sharing between paired client devices, information sharing between client device 102A and its MEC server run by a mobile operator, information sharing between MEC servers 108 within the proximity of client device 102A using an MEC module 226, and information sharing to a cloud server using a cloud module 228.

SDK 106 also provides a platform for plurality of client devices 102A-102N to connect and share any data after they are clustered based on the Received Signal Strength Indicator (RSSI) they receive using a clustering module 230. Clustering module 230 groups Wi-Fi users under the criterion of receiving signal from the same Wi-Fi access point. Wi-Fi users in a network might receive signals from different Wi-Fi access points and share the data with other stations/client devices when they encounter a unique Wi-Fi access point. The users can track distribution of their data and the number of users to which they have delivered their data through this platform.

In accordance with an exemplary implementation, SDK 106 is used for contact tracing to help authorities during an epidemic/pandemic outbreak to decelerate any epidemic efficiently, by tracking past and present contacts of infected patients, monitoring human mobility in real time, and creating a predictive risk mapping using population-based travel data.

Mobility pattern determination/monitoring module 214 monitors mobility patterns of a client device 102A of plurality of client devices 102A-102N for the past x days depending on the incubation period of the virus and stores the mobility patterns in the local memory of client device 102A. This process is performed by client device 102A itself based on Wi-Fi signal measurements/recordings of Wi-Fi access points, Wi-Fi based sniffing to detect other client devices in vicinity of client device 102A and/or GPS tracking. In this way, even indoors, room by room or floor by floor contact monitoring/tracing can be performed with higher accuracy, less power consumption, and reduced data transmission.

Mobility patterns of client device 102A which includes the location information that client device 102A has traveled for the past x days is shared both with authorities and the paired client devices in case user/owner of client device 102A is marked manually as a confirmed/under-quarantine/infected case by the authorities, or in case the user marks himself/herself as under-quarantine, or in case the user is in a place/area that is not approved/allowed by the authorities. In these cases, the information is shared to other users in the vicinity of client device 102A either by client device 102A itself via Wi-Fi access points or ad-hoc communication between client devices, or by MEC servers 108 located close to client device 102A. The information is also sent to/stored on cloud 110 and is accessible only to relevant authorities.

Using mobility pattern determination/monitoring module 214, authorities can effectively track each user's mobility pattern in case of an alert, such as when a curfew is declared, or in case a user is in a place/area that is restricted by the authorities. In this way, a user who does not follow the rules can be traced, sanctioned, or quarantined by the authorities to be able to control the epidemic and slow down the rate of its spread. Mobility pattern determination/monitoring module 214 further enables the authorities to prevent possible clutter/congestion by specifying/separating the places where each user can go, with a specific time zone.

Security and privacy module 222 encrypts any data captured by SDK 106 and stores it locally on client device 102A for x days, which spans the incubation period of the virus. Data is shared securely only in case owner/user of client device 102A is infected. Data logs are stored locally on client device 102A with cryptographically generated temporary IDs. The data logs are extracted only when needed by the authorities for contact tracing. Refusal to provide such data when requested might result in individuals being prosecuted under the country's Infectious Diseases Act. When needed in contact tracing, users of plurality of client devices 102A-102N will have to authorize the uploading of their data to the Ministry of Health, which will then assess the information and retrieve the mobile numbers of close contacts of these client devices within that period of time.

Moving on, contact identification and tracing module 216 is responsible for deciding what kind of information is to be stored on client device 102A, and to where the data is to be transferred from client device 102A. In this context, contact identification and tracing module 216 holds information such as, but not limited to, MAC addresses of paired client devices, their mobile numbers if available and other data related to users of each paired device such as, but not limited to, age, gender, nationality of users, and where he/she visited.

In case owner of client device 102A is a confirmed/infected/under-quarantine case, information related to the owner is shared with others in the different ways using information sharing module 224. These include, but need not be limited to, information sharing between paired devices, information sharing between client device 102A and its MEC server run by the mobile operator, information sharing between MEC servers 108 within the proximity of client device 102A using MEC module 226, and information sharing to the cloud server using cloud module 228. The process of information sharing complies with the Personal Data Protection Law (PDPL) and the General Data Protection Regulation (GDPR).

The information is first shared with other users who are paired with client device 102A which is marked as an infected or under-quarantine case. This information is also shared with MEC servers 108, which is run by the mobile operator of client device 102A, located within the coverage of client device 102A. Thus, it will be ensured that the information pertaining to infection risk is transferred to other client devices in the vicinity of client device 102A or to client devices that will be in the vicinity of client device 102A in future.

MEC servers 108 then share this information with its neighboring MEC servers so that any client device using any mobile operator will be able to receive the information of infection risk when in the vicinity. The information is also uploaded/stored on cloud 110 and is accessible only to relevant authorities, so that contact tracing can be efficiently handled by the authorities. Using MEC module 226, the information of the infected user is transmitted to the user's base station and other base stations in the vicinity. In this way, users who are in the vicinity of the risky area or users approaching this region may be alerted via local MEC servers on base stations. Further, local users are provided with information about the risk of infection through MEC servers 108. In this way, when any case is identified manually, information is sent to client devices located within the area for the last x days, which is the incubation period of the virus. Thus, all client devices in the risky area are locally alerted.

Further, contact identification and tracing module 216 enables client device 102A maintain a list of one or more Wi-Fi access points it hears and is connected to, in its local memory based on recording and analyzing and past and current signal data/measurements of the one or more Wi-Fi access points and mobility patterns of client device 102A. In case the owner of client device 102A is infected, client devoice 102A is marked by the doctor in the hospital, or an authorized person through SDK 106, and after this marking, client device 102A sends the list it holds to the other client devices connected to the same Wi-Fi access points at that time through the cloud using cloud module 228, and each client device then calculate its own infection probability.

SDK 106 also includes a heat/risk map module 232 for creating dynamic heat maps to track the spread of the virus, and also to identify and predict places where infected patients had passed or are likely to pass based on measurements of Wi-Fi access points recorded in the local memory of the respective client devices and Wi-Fi access point-based localization, using Wi-Fi access point and user localization module 218. Using Wi-Fi access point and user localization module 218, locations are assigned to Wi-Fi access points and users based on a small number of GPS samples from client devices of the users, and these Wi-Fi access points are used as fixed beacons to predict other users' locations.

Wi-Fi access point and user localization module 218 provides the exact location of each Wi-Fi access point, whether public or private, in environments where there are public Wi-Fi hotspots available such as cafes, malls, and buses, where infection transmission is likely to take place. This information is then used by heat/risk map module 232 to realistically position the infected cases, under-quarantine cases, and other client devices that client devices of infected cases pair with, on the heat map. Since a whole range of inputs including, but not limited to, symptoms and demographic factors are considered in addition to mobility patterns to calculate risk factors, creating dynamic heat maps with case positioning is vital to identify and predict places where infected patients are likely to pass.

Through the heat map, infected users' locations with additional information such as, but not limited to, age, gender, nationality, and locations the users visited may also be shared locally or globally with the consent from authorities only with other users within close proximity. In this way, a whole range of inputs including, but not limited to, symptoms and demographic factors are considered in addition to mobility patterns to calculate risk factors.

Heat/risk map module 232 further includes a coloring module 234 which enables different cases to be shown on the heat map with different colors. For instance, client devices that an infected client device pairs with are depicted in yellow color, under self-quarantine cases are depicted in blue color, and the infected cases are depicted in red color on the heat map. Yellow color may be used to depict either the current locations of client devices, or locations where they encounter infected ones.

Figure 3:
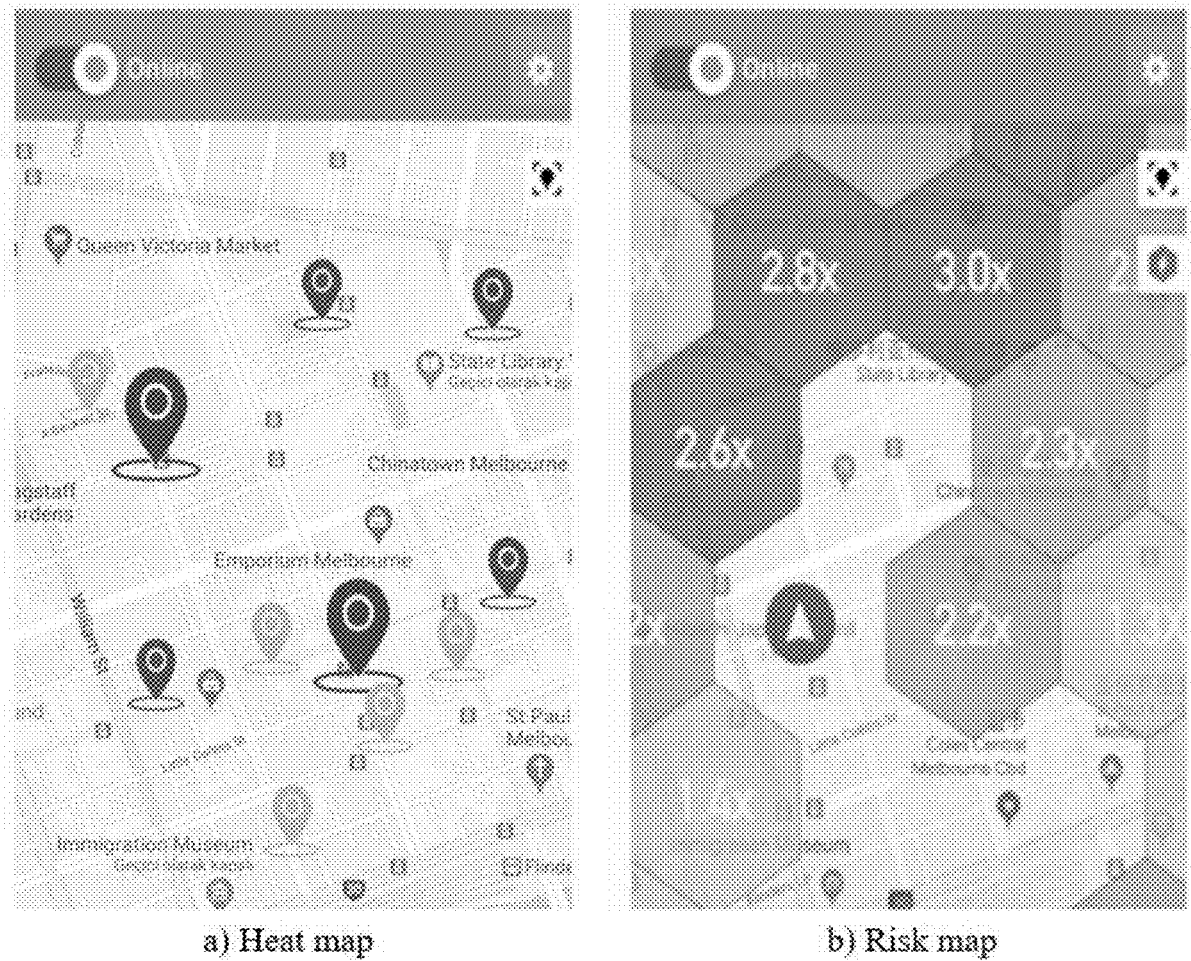
FIG. 3 illustrates heat and risk maps created by a heat/risk map module of the SDK in accordance with an embodiment of the invention.

Apart from the three colors on the heat map, potential risk ratios of every region are also determined by a risk map generated by heat/risk map module 232. The risk map shows each sub-region on the map in different percentages and shades of red color according to their risk ratio using coloring module 234. With the help of this map, individuals can stop going to a specific region classified as a containment zone or update their routes according to risk ratios on the risk map. Sample images of heat and risk maps are illustrated in FIG. 3.

Furthermore, information about infected cases, their mobility patterns and information of other users with whom these infected cases are paired with are also stored in cloud 110 using cloud module 228. Access to this information is not public and only the authorities can access this data to slow the spread of epidemic outbreak with contact tracing. Marking service set identifiers (SSIDs)/client devices as infected or under quarantine also result in this information to be uploaded to cloud 110 for further contact tracing opportunity.

The data is kept anonymous in cloud 110, and access is available to authorized people unless otherwise specified. If the authorities provide their consent, individuals can view not only their own mobility patterns but also the mobility patterns of infected cases on a heat map, and other related data such as, but not limited to, specific places each user can visit, with a specific time zone, to provide social distancing among people.

Using cloud module 228, information obtained from users, and their mobility pattern are first matched with the prohibitions/permissions entered by the authorities in the cloud. User-specific information such as, but not limited to, list of preferred/selected places to visit, time zones, and estimated crowd rate of selected places, are then transmitted to users to be able to guide or direct individuals with everyday errands, and to minimize interaction while maintaining social distancing.

During curfew or after pandemic when the business gradually reopens, a social distancing module 236 in conjunction with mobility pattern determination/monitoring module 214 and cloud module 228, may be used to guide or direct individuals with everyday errands to minimizing interaction while maintaining social distancing. For example, when a person specifies a requisite to go to a grocery store, social distancing module 236 identifies which grocery store they can immediately utilize or if they have a personal preference for a specific store, identifies at what time slot they can visit the store. In this way, social interaction can be minimized. Social distancing module 236 can also suggest which specific route or public transportation a person might take, collectively by collaborating with other users. Further, social distancing module 236 can be used for any general-purpose stores such as, but not limited to, pharmacy, mechanic, grocery stores, hairdresser, and coffee shops. Social distancing module 236 can also organize public transportation and traffic, by staggering work schedules. For example, social distancing module 236 may suggest that after pandemic some employees can start working 30 minutes early or later than their previous schedule to maintain social distancing in public transportation.

Figure 4:
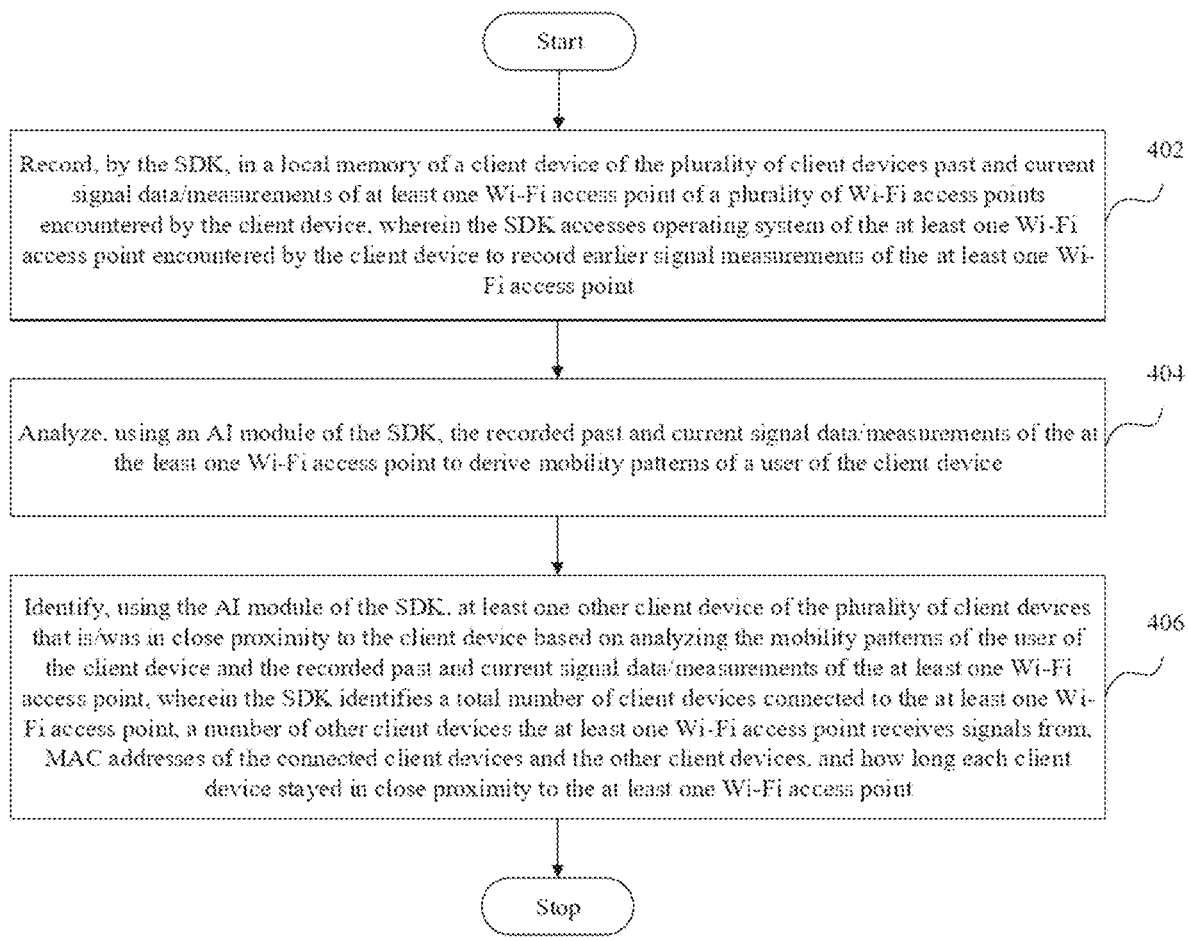
FIG. 4 illustrates a flowchart of a method for contact tracing using the SDK integrated into each client device of the plurality of client devices in accordance with an embodiment of the invention.

FIG. 4 illustrates a flowchart of a method for contact tracing using SDK 106 integrated into each client device of plurality of client devices 102A-102N in accordance with an embodiment of the invention.

As illustrated in FIG. 4, at step 402, SDK 106 records past and current signal data/measurements of one or more Wi-Fi access points of plurality of Wi-Fi access points 104A-104N encountered by client 102A in the local memory of client device 102A. SDK 106 further accesses operating system of the one or more Wi-Fi access points encountered by client device 102A to record earlier signal measurements of the one or more Wi-Fi access points.

In an ensuing step 404, AI module 212 of SDK 106 analyzes the recorded past and current signal data/measurements of the one or more Wi-Fi access points to derive mobility patterns of a user of client device 102A using mobility pattern determination/monitoring module 214.

Thereafter, at step 406, AI module 212 identifies one or more other client devices that is/was in close proximity to client device 102A based on analyzing the mobility patterns of the user of client device 102A and the recorded past and current signal data/measurements of the one or more Wi-Fi access points. Using AI module 212, SDK 106 is able to identify a total number of client devices connected to the one or more Wi-Fi access points, a number of client devices the one or more Wi-Fi access points receives signals from, MAC addresses of the client devices in close proximity to client device 102A, and how long each client device stayed in close proximity to the one or more Wi-Fi access points.

Contact identification and tracing module 216 enables client device 102A maintain a list of one or more Wi-Fi access points it hears and is connected to and a pairing list of client devices in its local memory based on processing/analyzing past and current signal data/measurements of the one or more Wi-Fi access points and mobility patterns of client device 102A.

Furthermore, for contact tracing, network sniffing module 220 performs sniffing over a wireless interface such as, but not limited to, Wi-Fi and Bluetooth to identify mobile/fixed users of one or more client devices of plurality of client devices 102A-102N in close proximity/vicinity to client device 102A but not connected to the same Wi-Fi access point as client device 102A. Recording module 210 then records the information related to the one or more client devices in the local memory of client device 102A if received signal strength from the one or more client devices exceeds a predetermined threshold value. Further, if only the received signal strength obtained from other client devices in the vicinity while performing the sniffing operation on the Wi-Fi interface is above a threshold value, contact identification and tracing module 216 includes these client devices in the pairing group and stores information related to those client devices in its local memory using recording module 210.

The present invention is advantageous in that the SDK provided by the invention is easy to launch across governments, service providers and enterprise infrastructures. The SDK can be easily integrated into any client device application (mobile application) in use and does not require significant time or cost to set up. The SDK can also complement collecting location data through GPS as using GPS data to locate mobile phone users at a large scale may create noise leading to reduced efficiency and false positives. This helps in achieving greater accuracy and efficiency in contact tracing, collecting location data in environments where infection transmission is more likely to take place.

Furthermore, the SDK of the present invention enables case and contact identification, which is critical for effective epidemic monitoring and response, and vital for governments to provide clear information to prevent panic in society. Also, the invention can help governments trace trajectories and contacts of infected cases across space and time.

The present invention also complies with the PDPL and the GDPR. In short, each client device keeps a list of Wi-Fi access points it hears and is connected to, in its local memory using the SDK. In case the owner of the device is infected, the device is marked by a doctor in the hospital, or an authorized person through the SDK, and after this marking, the client device sends the list it holds to the other devices connected to the same Wi-Fi access points at that time through the cloud, and each device then calculates its own infection probability.

Consequently, the unique approach of the present invention not only integrates widespread Wi-Fi access points with sniffing vicinity to visualize infected persons' locations on a heat map to build an effective dashboard for authorities, but also provides minimized social interaction among people while maintaining their daily lives. In this way, not only does the management system yield more effective results but is also extremely flexible. It opens multiple technology adaptations and collaboration opportunities with authorities that can shorten timely critical decision-making processes while providing crucial inputs for epidemic mitigation frameworks set up by the World Health Organization (WHO).

Those skilled in the art will realize that the above recognized advantages and other advantages described herein are merely exemplary and are not meant to be a complete rendering of all of the advantages of the various embodiments of the present invention.

The system, as described in the invention or any of its components may be embodied in the form of a computing device. The computing device can be, for example, but not limited to, a general-purpose computer, a programmed microprocessor, a micro-controller, a peripheral integrated circuit element, and other devices or arrangements of devices, which are capable of implementing the steps that constitute the method of the invention. The computing device includes a processor, a memory, a nonvolatile data storage, a display, and a user interface.

In the foregoing specification, specific embodiments of the present invention have been described. However, one of ordinary skill in the art appreciates that various modifications and changes can be made without departing from the scope of the present invention. Accordingly, the specification and figures are to be regarded in an illustrative rather than a restrictive sense, and all such modifications are intended to be included within the scope of the present invention.

What is claimed is:

1. A method for contact tracing using a Software Development Kit (SDK) integrated into each client device of a plurality of client devices, the method comprising: recording, by the SDK, in a local memory of a client device of the plurality of client devices past and current signal data/measurements of at least one Wi-Fi access point of a plurality of Wi-Fi access points encountered by the client device, wherein the SDK accesses operating system of the at least one Wi-Fi access point encountered by the client device to record earlier signal measurements of the at least one Wi-Fi access point; analyzing, using an Artificial Intelligence (AI) module of the SDK, the recorded past and current signal data/measurements of the at the least one Wi-Fi access point to derive mobility patterns of a user of the client device; and identifying, using the AI module of the SDK, at least one other client device of the plurality of client devices that is/was in close proximity to the client device based on analyzing the mobility patterns of the user of the client device and the recorded past and current signal data/measurements of the at least one Wi-Fi access point, wherein the SDK identifies a total number of client devices connected to the at least one Wi-Fi access point, a number of other client devices the at least one Wi-Fi access point receives signals from, MAC addresses of the connected client devices and the other client devices, and how long each client device stayed in close proximity to the at least one Wi-Fi access point.

2. The method of claim 1, wherein the recording further comprises performing sniffing, by the SDK over a Wi-Fi interface to identify mobile/fixed users of at least one other client device in close proximity/vicinity to the client device but not connected to the same Wi-Fi access point as the client device, and recording, by the SDK, the information related to the at least one other client device in the local memory of the client device if received signal strength from the at least one other client device exceeds a predetermined threshold value.

3. The method of claim 1, wherein the identifying further comprises assigning locations, by the SDK, to the at least one Wi-Fi access point encountered by the client device based on a small number of GPS samples taken from the at least one other client device.

4. The method of claim 1 further comprises pairing, using the AI module of the SDK, users of client devices that are in the vicinity of the same Wi-Fi access point with respect to certain time periods, for receiving/transmitting information for the purpose of contact tracing.

5. The method of claim 4 further comprises informing, by the SDK, other client devices that a client device was paired with in the past based on measurements from Wi-Fi access points and Wi-Fi sniffing with respect to certain time periods, after the client device is marked as confirmed/infected/under-quarantine by an authorized person during an epidemic/pandemic outbreak, wherein the authorized person is at least one of a doctor and a relevant health authority.

6. The method of claim 5 further comprises transmitting information related to the user of the client device marked as confirmed/infected/under-quarantine, to relevant entities via at least one of the client device itself and Mobile Edge Computing (MEC) servers located in close proximity to the client device, wherein an entity is at least one of a health authority and a cloud platform, wherein the information comprises at least one of an age, gender, nationality and locations visited.

7. The method of claim 6, wherein the transmitting further comprises sending information from the client device marked as confirmed/infected/under-quarantine to other client devices connected to the same Wi-Fi access point as the client device using the cloud platform, and upon receiving the information, each of the other client devices calculates probability of infection, wherein the information comprises at least one of details of the user of the client device and a list of Wi-Fi access points that the client device had encountered and/or is connected to as recorded in the local memory of the client device.

8. The method of claim 5 further comprises creating, using the SDK, dynamic heat maps to track the spread of an infection and identify and predict locations where infected users are likely to pass, based on measurements of Wi-Fi access points recorded in the local memory of the client device and Wi-Fi access point-based localization.

9. The method of claim 5 further comprises maintaining social distancing by enabling the collaboration between users of client devices and one or more authorities via the SDK, wherein the collaboration comprises obtaining information from the users of the client devices, and matching their mobility patterns with the prohibitions/permissions entered by the one or more authorities in the cloud platform.

10. The method of claim 9 further comprises transmitting relevant information to the users to guide or direct the users and to minimize interaction while maintaining social distancing, wherein the information comprises at least one of list of preferred/selected places to visit, time zones, and estimated crowd rate of selected places.

11. A system for contact tracing using a Software Development Kit (SDK) integrated into each client device of a plurality of client devices, the system comprising: a memory; a processor communicatively coupled to the memory, wherein the processor is configured to: record, by the SDK, in a local memory of a client device of the plurality of client devices past and current signal data/measurements of at least one Wi-Fi access point of a plurality of Wi-Fi access points encountered by the client device, wherein the SDK accesses operating system of the at least one Wi-Fi access point encountered by the client device to record earlier signal measurements of the at least one Wi-Fi access point; analyze, using an Artificial Intelligence (AI) module of the SDK, the recorded past and current signal data/measurements of the at the least one Wi-Fi access point to derive mobility patterns of a user of the client device; and identify, using the AI module of the SDK, at least one other client device of the plurality of client devices that is/was in close proximity to the client device based on analyzing the mobility patterns of the user of the client device and the recorded past and current signal data/measurements of the at least one Wi-Fi access point, wherein the SDK identifies a total number of client devices connected to the at least one Wi-Fi access point, a number of other client devices the at least one Wi-Fi access point receives signals from, MAC addresses of the connected client devices and the other client devices, and how long each client device stayed in close proximity to the at least one Wi-Fi access point.

12. The system of claim 11, wherein the processor is configured to perform sniffing, by the SDK over a Wi-Fi interface to identify mobile/fixed users of at least one other client device in close proximity/vicinity to the client device but not connected to the same Wi-Fi access point as the client device, and recording, by the SDK, the information related to the at least one other client device in the local memory of the client device if received signal strength from the at least one other client device exceeds a predetermined threshold value.

13. The system of claim 11, wherein the processor is configured to assign locations, by the SDK, to the at least one Wi-Fi access point encountered by the client device based on a small number of GPS samples taken from the at least one other client device.

14. The system of claim 11, wherein the processor is further configured to pair, using the AI module of the SDK, users of client devices that are in the vicinity of the same Wi-Fi access point with respect to certain time periods, for receiving/transmitting information for the purpose of contact tracing.

15. The system of claim 14, wherein the processor is further configured to inform, by the SDK, other client devices that a client device was paired with in the past based on measurements from Wi-Fi access points and Wi-Fi sniffing with respect to certain time periods, after the client device is marked as confirmed/infected/under-quarantine by an authorized person during an epidemic/pandemic outbreak, wherein the authorized person is at least one of a doctor and a relevant health authority.

16. The system of claim 15, wherein the processor is configured to transmit information related to the user of the client device marked as confirmed/infected/under-quarantine, to relevant entities via at least one of the client device itself and Mobile Edge Computing (MEC) servers located in close proximity to the client device, wherein an entity is at least one of a health authority and a cloud platform, wherein the information comprises at least one of an age, gender, nationality and locations visited.

17. The system of claim 16, wherein the processor is configured to send information from the client device marked as confirmed/infected/under-quarantine to other client devices connected to the same Wi-Fi access point as the client device using the cloud platform, and upon receiving the information, each of the other client devices calculates probability of infection, wherein the information comprises at least one of details of the user of the client device and a list of Wi-Fi access points that the client device had encountered and/or is connected to as recorded in the local memory of the client device.

18. The system of claim 15, wherein the processor is further configured to create, using the SDK, dynamic heat maps to track the spread of an infection and identify and predict locations where infected users are likely to pass, based on measurements of Wi-Fi access points recorded in the local memory of the client device and Wi-Fi access point-based localization.

19. The system of claim 15, wherein the processor is configured to maintain social distancing by enabling the collaboration between users of client devices and one or more authorities via the SDK, wherein the collaboration comprises obtaining information from the users of the client devices, and matching their mobility patterns with the prohibitions/permissions entered by the one or more authorities in the cloud platform.

20. The system of claim 19, wherein the processor is configured to transmit relevant information to the users to guide or direct the users and to minimize interaction while maintaining social distancing, wherein the information comprises at least one of list of preferred/selected places to visit, time zones, and estimated crowd rate of selected places.

* * * * *